United States Patent [19]

Zipplies et al.

[11] Patent Number: 5,095,021
[45] Date of Patent: Mar. 10, 1992

[54] PHENYLALKYLAMINES AND FUNGICIDES CONTAINING THESE

[75] Inventors: Matthias Zipplies, Hirschberg; Ernst Buschmann; Eberhard Ammermann, both of Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 692,972

[22] Filed: Apr. 29, 1991

Related U.S. Application Data

[63] Continuation of Ser. No. 451,872, Dec. 18, 1989, abandoned.

[30] Foreign Application Priority Data

Jan. 18, 1989 [DE] Fed. Rep. of Germany ....... 3901244

[51] Int. Cl.$^5$ ............... A61K 31/435; A61K 31/33; C07D 211/08; C07D 265/30
[52] U.S. Cl. ..................... 514/317; 514/319; 514/327; 514/239.2; 514/239.5; 514/238.8; 544/173; 544/174; 544/177; 544/178; 544/192; 544/205; 544/206; 544/216; 544/217; 544/236
[58] Field of Search ............. 546/192, 216, 217, 205, 546/206, 236; 514/317, 327, 319

[56] References Cited

U.S. PATENT DOCUMENTS 4,705,553 11/1987 Buschmann et al. ............ 544/178

FOREIGN PATENT DOCUMENTS 164706 6/1984 European Pat. Off. ........... 544/178

Primary Examiner—Johann Richter
Attorney, Agent, or Firm—Oblon, Spivak, McClelland, Maier & Neustadt

[57] ABSTRACT

Phenylalkylamines of the formula

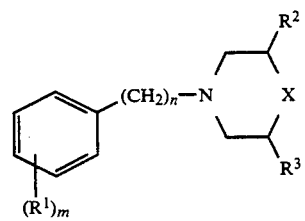

where n is 5, 6, 7, 8 or 9, m is 1, 2 or 3, $R^1$ is methyl, halogen, substituted or unsubstituted aryl or substituted or unsubstituted phenoxy, and, when m is 2, two adjacent radicals $R^1$ together denote the radical

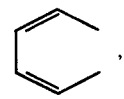

X is oxygen, except when $R^1$ is methyl, or the radical

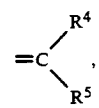

$R^4$ is isopropyl, tert-butyl or substituted or unsubstituted phenyl and $R^5$ is H or OH, $R^2$ and $R^3$ are each hydrogen and, when X is oxygen, $R^2$ and $R^3$ additionally denote methyl or ethyl, and their plant-tolerated salts, and fungicides containing these compounds.

16 Claims, No Drawings

PHENYLALKYLAMINES AND FUNGICIDES CONTAINING THESE

This application is a continuation of application Ser. No. 07/451,872 filed on Dec. 18, 1989, now abandoned.

BACKGROUND OF THE INVENTION

The present invention relates to phenylalkylamines (-morpholines, -piperidines), fungicides containing these and methods for controlling fungi with these compounds.

FIELD OF THE INVENTION

EP 164,706 discloses compound II as substance having plant growth-regulating properties.

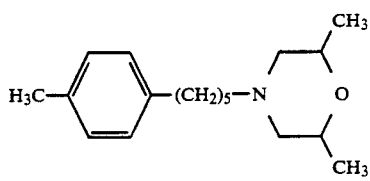

DISCUSSION OF THE BACKGROUND

No fungicidal activity of the compound is described. We have now found that phenylalkylamines of the general formula

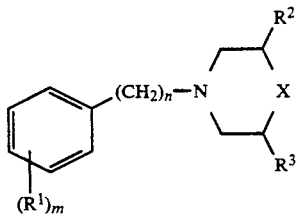

where
n is 5, 6, 7, 8 or 9,
m is 1, 2 or 3,
$R^1$ is methyl, 4-monohalo, 2,4-dihalo or 2,4,6-trihalo, or aryl or phenoxy each of which is substituted or unsubstituted,
furthermore when m=2 two adjacent $R^1$ radicals are together

X is oxygen except when $R^1$ is methyl or
X is

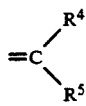

$R^4$ is isopropyl, tert.-butyl or phenyl which is substituted or unsubstituted, and
$R^5$ is H or OH,
$R^2$, $R^3$ are hydrogen and, in the case where X is oxygen, $R^2$ and $R^3$ are additionally methyl or ethyl, as well as the salts thereof which are tolerated by plants, have an excellent fungicidal action against phytopathogenic fungi and, moreover, have no phytotoxic action.

Examples of $R^1$ are halogen (Cl, Br, I) or aryl (phenyl) which is unsubstituted or substituted up to three times by $C_1$-$C_4$-alkoxy (methoxy), or $R^1$ is phenoxy which is unsubstituted or substituted up to three times by $C_1$-$C_4$-alkyl (methyl), halogen, $C_1$-$C_4$-alkoxy (methoxy). When m=2, two adjacent $R^1$ radicals together are, for example,

i.e. together with phenyl they are naphthyl

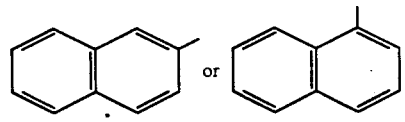

Examples of $R^4$ are phenyl which is unsubstituted or substituted up to three times by $C_1$-$C_4$-alkyl (methyl), halogen, $C_1$-$C_4$-alkoxy (methoxy).

Salts are defined as salts with any desired protonic acids, inorganic and organic acids, e.g. with hydrogen chloride, hydrofluoric acid, hydrogen bromide, sulfuric acid, phosphoric acid, hydroiodic acid, dodecylbenzenesulfonic acid, formic acid, alkylcarboxylic acid, acetic acid, propionic acid, palmitic acid, perfluoroheptanoic acid, oxalic acid, malonic acid, benzoic acid, malic acid, dodecyl sulfuric acid, glycerol-2-phosphoric acid, methyl sulfuric acid, methylsulfonic acid, p-toluenesulfonic acid, nitric acid, 2,6-dichloroisonicotinic acid, saccharin, as well as, for example, hydrogen sulfates and dihydrogen phosphates.

Some of the novel phenylalkylamines of the formula I contain chiral centers. Preparation thereof generally results in racemates or, where appropriate, mixtures of diastereomers.

In the case of some of the novel compounds, pure diastereomeric compounds can be isolated by, for example, distillation, column chromatography or on the basis of solubility differences. Enantiomerically pure compounds can be obtained, for example, by racemate resolution with a chiral reagent by conventional methods, for example via diastereomeric salts. Suitable for use of the novel phenylalkylamines as fungicides are both the diastereomers and the enantiomers, as well as the mixtures of stereoisomers thereof produced in the synthesis. The invention embraces all of them.

The cis-dialkyl derivatives of 2,6-dialkylmorpholino

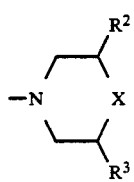

are particularly preferred.

The compounds I according to the invention can be prepared in a conventional manner (equation 1)

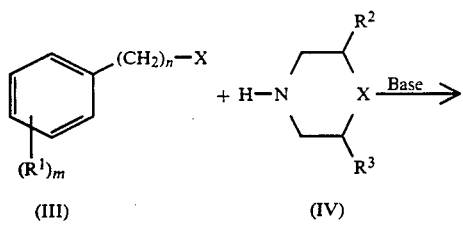

(III)    (IV)

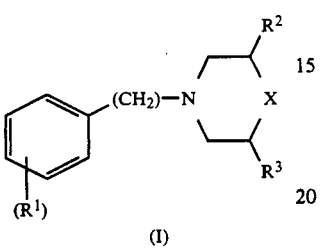

(I)

by reacting a suitable phenylalkyl compound of the structure III, where X is a leaving group amenable to nucleophilic substitution, such as chlorine, bromine, methyl or toluenesulfonyl, with a suitably substituted secondary amine of the structure IV in the presence of a base and, where appropriate, in the presence of a solvent, and isolating the reaction product in a conventional manner.

Examples of suitable solvents are tetrahydrofuran, acetonitrile, toluene, xylene, DMF, methanol, dimethyl sulfoxide. The reaction is advantageously carried out at from 50° to 200° C. Examples of suitable bases are $Na_2CO_3$, $K_2CO_3$, $NaHCO_3$, triethylamine or else an excess of the secondary amine IV.

The phenylalkyl halides of the general structure III which are required as precursors can be prepared in a conventional manner by the linkage, catalyzed by lithium cuprate, of aryl- or arylalkyl-Grignard compounds with dihaloalkanes V (equation 2). HAL=Cl, Br.

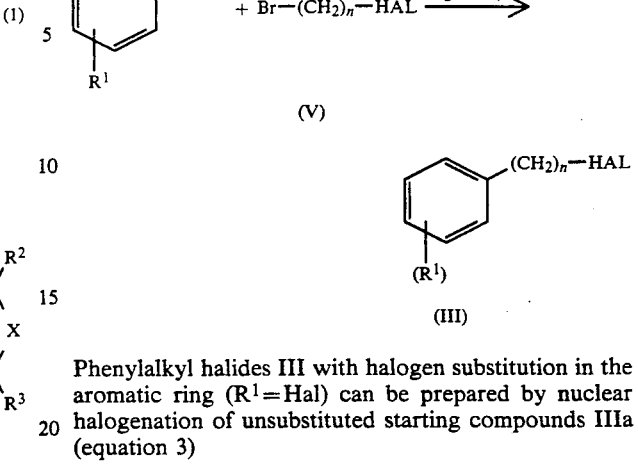

Phenylalkyl halides III with halogen substitution in the aromatic ring ($R^1$=Hal) can be prepared by nuclear halogenation of unsubstituted starting compounds IIIa (equation 3)

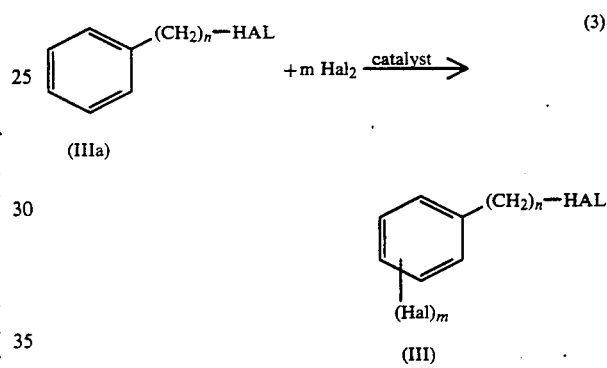

as well as by the general reaction sequence shown in equation 4 (cf. A. J. Hubert, J. Chem. Soc. C (1967) 235).

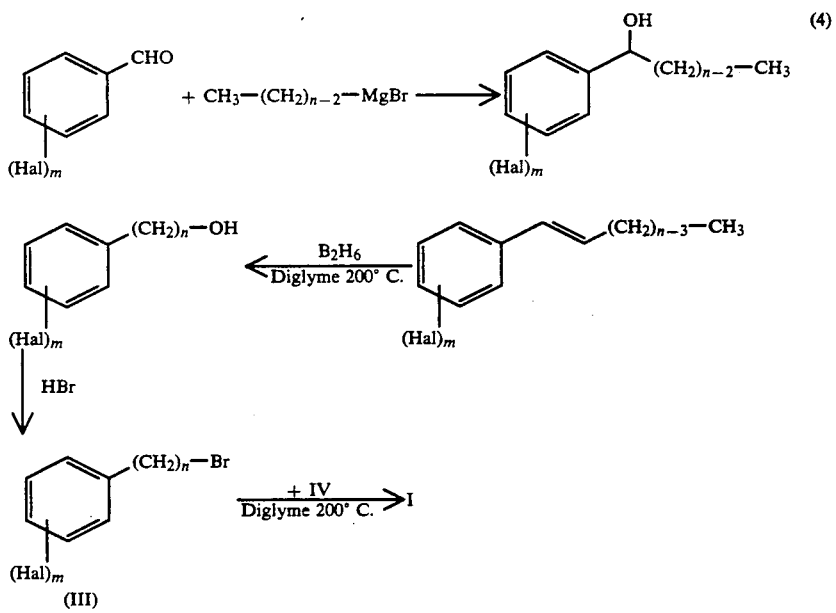

Nuclear-iodinated precursors I ($R^1$=iodine) can be prepared, for example, by the general method of Suzuki (Bull. Chem. Soc. Jap. 39 (1966) 128) (equation 5).

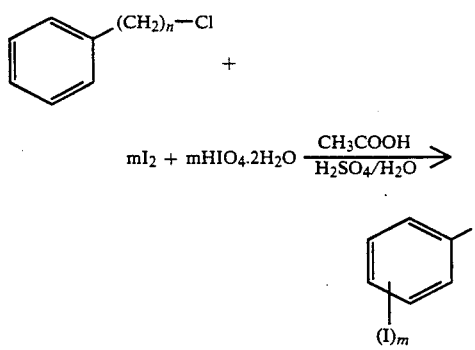

Example of the preparation of a precursor 5-(4-Tolyl)-pentyl bromide

A Grignard solution prepared from 148 g (0.87 mol) of 4-bromotoluene in 520 ml of absolute tetrahydrofuran and 22 g (0.92 mol) of magnesium turnings is added dropwise at from −5° to 0° C. to a stirred mixture of 300 g (1.3 mol) of 1,5-dibromopentane, 1.5 g of LiCl and 3.0 g of CuCl₂ in 480 ml of absolute tetrahydrofuran under nitrogen in 2 h. The mixture is then stirred at room temperature for 1 h, 1100 ml of saturated NH₄Cl solution are added, and the mixture is stirred at room temperature (20° C.) overnight and extracted with ether. The ether phase is washed, dried, concentrated and distilled under reduced pressure (140°–45° C./3.5 mbar): 79.6 g (38% of theory).

A large number of other precursors of the general structure III can be prepared in a similar manner. Examples of preparations of novel compounds

EXAMPLE 1

N-[8-(4-Tolyl)octyl]-4-hydroxy-4-phenylpiperidine (compound No. 1)

10 g (40 mmol) of 1-chloro-8-tolyloctane, 21.2 g (120 mmol) of 4-hydroxy-4-phenylpiperidine, 5.52 g (40 mmol) of potassium carbonate and 3.3 g (20 mmol) of potassium iodide are heated with 30 ml of xylene at 160° C. for 8 h. The solvent is removed by distillation under reduced pressure. The residue is taken up in dichloromethane/dilute sodium hydroxide solution, and the organic extract is worked up in a conventional manner. The low-boiling compounds are removed by distillation under reduced pressure up to 150° C./0.9 mbar. 11.4 g (94%) of a resin are obtained (see Tab. 1 for physical data).

The novel compounds of the formula I listed in Table 1 can be prepared in the specified manner.

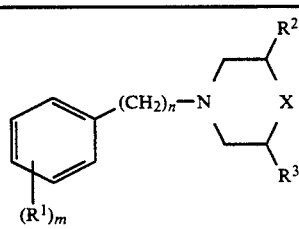

| Comp. No. | $(R^1)_m$ | n | X | $R^2$ | $R^3$ | M.p. (°C.)b.p.(°C./mbar) Comments IR(cm⁻¹) |
|---|---|---|---|---|---|---|
| 1 | 4-CH₃ | 8 | C₆H₅–CH< | H | H | 2924, 2849, 1975, 1378, 1110, 1042, 811, 758, 697, 547 |
| 2 | 4-CH₃ | 5 | tert-butyl-CH< | H | H | 150/0.5 |
| 3 | 4-CH₃ | 8 | tert-butyl-CH< | H | H | 2921, 2850, 1515, 1463, 1450, 1364, 1124, 806, 491 |
| 4 | 2,4-Br₂ | 5 | tert-butyl-CH< | H | H | 2940, 2861, 2802, 2767, 1467, 1393, 1377, 1364, 1126, 808 |
| 5 | 4-Br | 5 | tert-butyl-CH< | H | H | 2923, 2855, 2800, 2764, 1487, 1467, 1443, 1122, 1353, 1040 |
| 6 | 4-J | 5 | tert-butyl-CH< | H | H | 2962, 2942, 2934, 2855, 2646, hydrochloride 2504, 1485, 1474, 1467, 1007 |

-continued
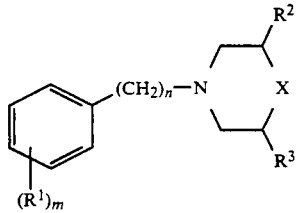
I
| Comp. No. | $(R^1)_m$ | n | X | $R^2$ | $R^3$ | M.p. (°C.) b.p. (°C./mbar) Comments IR(cm$^{-1}$) |
|---|---|---|---|---|---|---|
| 7 | 2,4-J$_2$ | 5 | tert-butyl-CH | H | H | 2956, 2854, 2715, 2640, 2571, 2498, 1456, 1437, 1394, 1363 hydrochloride |
| 8 | 2,4,6-(CH$_3$)$_3$ | 5 | tert-butyl-CH | H | H | 2942, 2860, 2801, 2767, 1480, 1468, 1376, 1364, 1127, 850 |
| 9 | 4-C$_6$H$_5$ | 5 | tert-butyl-CH | CH$_3$ | CH$_3$ | 152/0.2 |
| 10 | 4-Br | 5 | O | CH$_3$ | CH$_3$ | 162/0.15 |
| 11 | 2,4-Br$_2$ | 5 | O | CH$_3$ | CH$_3$ | 162/0.15 |
| 12 | 4-J | 5 | O | CH$_3$ | CH$_3$ | 160/0.2 |
| 13 | 4-C$_6$H$_5$ | 5 | O | H | H | 2933, 2854, 2806, 1986, 1448, 1135, 1119, 868, 762, 698 |
| 14 | cyclohexadienyl | 5 | O | CH$_3$ | CH$_3$ | 2970, 2933, 2857, 2811, 2773, 1323, 1145, 1086, 816, 746 |
| 15 | 4-CH$_3$ | 5 | C(C$_6$H$_5$)(OH) | H | H | 65 |
| 16 | 2,4-Br$_2$ | 5 | C(C$_6$H$_5$)(OH) | H | H | 2939, 2858, 2822, 1464, 1446, 1377, 1118, 1045, 761, 700 |
| 17 | 3,4-(CH$_3$)$_2$ | 5 | C(C$_6$H$_5$)(OH) | H | H | 2927, 2850, 2823, 1469, 1445, 1381, 1113, 1009, 760, 698 |
| 18 | 2,4,6-(CH$_3$)$_3$ | 5 | C(C$_6$H$_5$)(OH) | H | H | 85–88 |

-continued
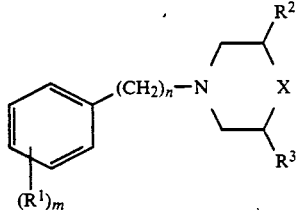
| Comp. No. | $(R^1)_m$ | n | X | $R^2$ | $R^3$ | M.p. (°C.)b.p.(°C./mbar) Comments IR(cm$^{-1}$) |
|---|---|---|---|---|---|---|
| 19 | 4-C$_6$H$_5$ | 5 | C(C$_6$H$_5$)OH | H | H | 78–80 |
| 20 | 2-CH$_3$ | 5 | CH(tert-butyl) | H | H | 180/0.2 |
| 21 | 2-CH$_3$ | 5 | C(C$_6$H$_5$)OH | H | H | resin 2939, 2917, 2818, 1460, 1443, 1145, 1045, 760, 738, 703 |
| 22 | 2,4-Cl$_2$ | 5 | O | CH$_3$ | CH$_3$ | 144/0.2 |
| 23 | 2,4-Cl$_2$ | 5 | CH(tert-butyl) | H | H | 151/0.2 |
| 24 | 2,4,6-Br$_3$ | 5 | O | CH$_3$ | CH$_3$ | 99–101 |
| 25 | 2,4-Cl$_2$ | 5 | C(C$_6$H$_5$)OH | H | H | 80–85 |
| 26 | 4-C$_6$H$_5$—O | 5 | O | CH$_3$ | CH$_3$ | 180/0.2 |
| 27 | 4-C$_6$H$_5$—O | 5 | CH(tert-butyl) | H | H | 205/0.2 |
| 28 | 4-C$_6$H$_5$—O | 5 | CH—(4-tert-butyl-C$_6$H$_4$) | H | H | 2933, 2858, 1590, 1506, 1489, 1469, 1240, 871, 821, 691 |
| 29 | 4-C$_6$H$_5$—O | 5 | CH—C$_6$H$_5$ | H | H | 2932, 2855, 1590, 1506, 1489, 1239, 871, 755, 699, 691 |
| 30 | 4-C$_6$H$_5$—O | 5 | C(4-tert-butyl-C$_6$H$_4$)OH | H | H | 115 |

-continued
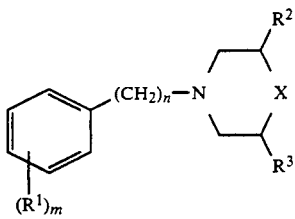
I
| Comp. No. | $(R^1)_m$ | n | X | $R^2$ | $R^3$ | M.p. (°C.)b.p.(°C./mbar) Comments IR(cm$^{-1}$) |
|---|---|---|---|---|---|---|
| 31 | 4-C$_6$H$_5$—O | 5 | ⌬–C(OH) | H | H | |
| 32 | 4-C$_6$H$_5$—O | 6 | ⌬–C(OH) | H | H | |
| 33 | 4-C$_6$H$_5$—O | 7 | ⌬–C(OH) | H | H | |
| 34 | 4-C$_6$H$_5$—O | 8 | ⌬–C(OH) | H | H | |
| 35 | 2,4-Cl$_2$ | 6 | ⌬–C(OH) | H | H | |
| 36 | 2,4-Cl$_2$ | 8 | ⌬–C(OH) | H | H | |
| 37 | 2,4-Cl$_2$ | 6 | O | CH$_3$ | CH$_3$ | |
| 38 | 2,4-Cl$_2$ | 8 | O | CH$_3$ | CH$_3$ | |
| 39 | 2,4-Cl$_2$ | 6 | CH(tert-butyl)(H) | H | H | |
| 40 | 2,4-Cl$_2$ | 8 | CH(tert-butyl)(H) | H | H | |
| 41 | 2,4-Br$_2$ | 6 | O | CH$_3$ | CH$_3$ | |
| 42 | 2,4-Br$_2$ | 8 | O | CH$_3$ | CH$_3$ | |

-continued $$\underset{(R^1)_m}{\underset{|}{\bigcirc}}-(CH_2)_n-N\underset{\diagdown}{\overset{\diagup}{\underset{\diagdown}{\bigg\langle}}}\overset{R^2}{\underset{R^3}{\overset{|}{X}}}\quad I$$

| Comp. No. | $(R^1)_m$ | n | X | $R^2$ | $R^3$ | M.p. (°C.)b.p.(°C./mbar) Comments IR(cm$^{-1}$) |
|---|---|---|---|---|---|---|
| 43 | 2,4-Br$_2$ | 6 | CH(tert-butyl)(H) | H | H | |
| 44 | 2,4-Br$_2$ | 8 | CH(tert-butyl)(H) | H | H | |
| 45 | 2,4-Br$_2$ | 6 | C(phenyl)(OH) | H | H | |
| 46 | 2,4-Br$_2$ | 8 | C(phenyl)(OH) | H | H | |
| 47 | 2,4-Br$_2$ | 5 | C(4-tert-butylphenyl)(OH) | H | H | |
| 48 | 2,4-Br$_2$ | 5 | CH(isopropyl)(H) | H | H | |
| 49 | cyclohexenyl | 5 | C(phenyl)(OH) | H | H | |
| 50 | cyclohexenyl | 6 | C(phenyl)(OH) | H | H | |

In general terms, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugarcane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 7 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 10 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 11 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 14 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 16 is intimately mixed with 97 parts by weight of particulate kaolin. A dust is obtained containing 3% by weight of the active ingredient.

VII. 30 parts by weight of compound no. 18 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 19 is intimately mixed with 10 parts of the sodium salt of a phenosulfonic acid-urea-formaldehyde condensate, 2 parts of silica gel and 48 parts of water to give a stable aqueous dispersion. Dilution in water gives an aqueous dispersion.

IX. 20 parts by weight of compound no. 23 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and N,N'-polypropylenebis(thiocarbamyl) disulfide;
nitro derivatives, such as dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as 2-heptadecylimidazol-2-yl acetate,
2,4-dichloro-6-(o-chloroanilino)-s-triazine,
O,O-dietyl phthalimidophospohonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
3 2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The active ingredients used for comparison purposes were N-5-(4-methylphenyl)-n-pentyl-2,6-dimethylmorpholine (A) (formula II, v. p. 1) disclosed in EP 164 706 and N-(3-(tert-butylphenyl)-2-methylpropyl)-cis-2,6-dimethylmorpholine (B) disclosed in DE-2 656 747.5.

USE EXAMPLE 1

Action on Cucumber Mildew (Curative)

Young cucumber plants of the "Chinesische Schlange" variety were sprayed at the two-leaf stage with an aqueous conidial suspension of barley mildew (Erysiphe cichoracearum and Sphaerotheca fuliginea). The next day these plants were sprayed to runoff with aqueous spray liquors consisting (dry basis) of 80% of active ingredient and 20% of emulsifier, and set up in the greenhouse at from 20° to 22° C. and a relative humidity of from 70 to 80%. The extent of fungus spread was assessed 21 days after the active ingredients had been applied.

The results show that active ingredients 2, 7, 10, 11, 14, 16, 18, 19, 23, 24, 26 and 29, applied as 0.025 wt % spray liquors, had a better fungicidal action (90%) than prior art comparative agents A (55%) and B (55%).

USE EXAMPLE 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 1, 2, 3, 4, 5, 6, 7, 9, 10, 12, 15, 16, 17, 19, 20, 21, 23, 25 and 28, applied as 0.05% spray liquors, had a better fungicidal action (90%) than prior art active ingredients A (70%) and B (55%).

We claim:

1. A phenylalkylamine of formula (I)

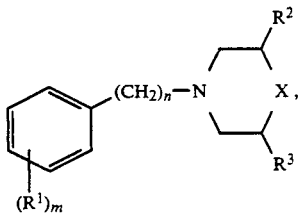

or a plant-tolerated salt thereof, wherein:
n is 5, 6, 7, 8 or 9:
m is 1, 2 or 3;
R₁ is methyl, halogen, unsubstituted aryl, aryl substituted by one to three C₁₋₄ alkoxy groups, unsubstituted phenoxy, or phenoxy substituted by one to three groups selected from the groups consisting of C₁₋₄ alkyl, halogen, and C₁₋₄ alkoxy, and, when m is 2, two adjacent radicals R¹ together denote a radical

X is the radical =CR⁴R⁵, wherein
R⁴ is isopropyl, tert-butyl, unsubstituted phenyl, or phenyl substituted by one to three groups selected from the group consisting of C₁₋₄-alkyl, halogen and C₁₋₄ alkoxy, and
R⁵ is H or OH;
R² and R³ are each hydrogen.

2. The phenylalkylamine of claim 1, wherein said aryl is phenyl.

3. The phenylalkylamine of claim 1, wherein said C₁₋₄ alkoxy is methoxy.

4. The phenylalkylamine of claim 1, wherein said C₁₋₄ alkyl is methyl.

5. A free phenylalkylamine in accordance with claim 1.

6. The phenylalkylamine of claim 1, wherein said plant-tolerated salt is a salt with hydrogen chloride, hydrofluoric acid, hydrogen bromide, sulfuric acid, phosphoric acid, hydroiodic acid, dodecylbenzenesulfonic acid, formic acid, alkylcarboxylic acid, acetic acid, propionic acid, palmitic acid, perfluoroheptanoic acid, oxalic acid, malonic acid, benzoic acid, malic acid, dodecyl sulfuric acid, glycerol-2-phosphoric acid, methyl sulfuric acid, methyl-sulfonic acid, p-toluenesulfonic acid, nitric acid, 2,6-dichloroisonicotinic acid, saccharin, a hydrogen sulfate, or a dihydrogen phosphate.

7. A fungicidal agent comprising a carrier and a fungicidally effective amount of a phenylalkylamine of formula (I)

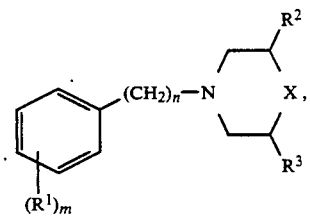

or a plant-tolerated salt thereof, wherein:
n is 5, 6, 7, 8 or 9:
m is 1, 2 or 3;
R₁ is methyl, halogen, unsubstituted aryl, aryl substituted by one to three C₁₋₄ alkoxy groups, unsubstituted phenoxy, or phenoxy substituted by one to three groups selected from the group consisting of C₁₋₄ alkyl, halogen, and C₁₋₄ alkoxy, and, when m is 2, two adjacent radicals R¹ together denote a radical

X is the radical =CR⁴R⁵, wherein
R⁴ is isopropyl, tert-butyl, unsubstituted phenyl, or phenyl substituted by one to three groups selected from the group consisting of C₁₋₄-alkyl, halogen and C₁₋₄ alkoxy, and
R⁵ is H or OH;
R² and R³ are each hydrogen.

8. The agent of claim 7, wherein said aryl is phenyl.

9. The agent of claim 7, wherein said C₁₋₄ alkoxy is methoxy.

10. The agent of claim 7, wherein said C₁₋₄ alkyl is methyl.

11. The agent of claim 7, wherein said plant-tolerated salt is a salt with hydrogen chloride, hydrofluoric acid, hydrogen bromide, sulfuric acid, phosphoric acid, hydroiodic acid, dodecylbenzenesulfonic acid, formic acid, alkylcarboxylic acid, acetic acid, propionic acid, palmitic acid, perfluoroheptanoic acid, oxalic acid, malonic acid, benzoic acid, malic acid, dodecyl sulfuric acid, glycerol-2-phosphoric acid, methyl sulfuric acid, methyl-sulfonic acid, p-toluenesulfonic acid, nitric acid, 2,6-dichloroisonicotinic acid, saccharin, a hydrogen sulfate, or a dihydrogen phosphate.

12. A method for combatting fungi comprising allowing a fungicidally effective amount of a phenylalkylamine of formula (I), or a plant-tolerated salt thereof, to act on the fungi, or materials, areas, plant or seed threatened by fungus attack, wherein said phenylalkylamine is a phenylalkylamine of formula (I)

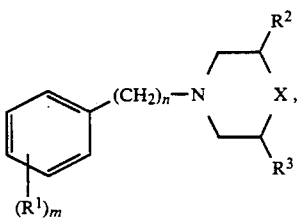

wherein:
n is 5, 6, 7, 8 or 9;
m is 1, 2 or 3;
$R_1$ is methyl, halogen, unsubstituted aryl, aryl substituted by one to three $C_{1-4}$ alkoxy groups, unsubstituted phenoxy, or phenoxy substituted by one to three groups selected from the group consisting of $C_{1-4}$ alkyl, halogen, and $C_{1-4}$ alkoxy, and, when m is 2, two adjacent radical $R^1$ together denote a radical

X is the radical $=CR^4R^5$, wherein
$R^4$ is isopropyl, tert-butyl, unsubstituted phenyl, or phenyl substituted by one to three groups selected from the group consisting of $C_{1-4}$-alkyl, halogen and $C_{1-4}$ alkoxy, and
$R^5$ is H or OH;
$R^2$ and $R^3$ are each hydrogen.

13. The method of claim 12, wherein said aryl is phenyl.

14. The method of claim 12, wherein said $C_{1-4}$ alkoxy is methoxy.

15. The method of claim 12, wherein said $C_{1-4}$ alkyl is methyl.

16. The method of claim 12, wherein said plant-tolerated salt is a salt with hydrogen chloride, hydrofluoric acid, hydrogen bromide, sulfuric acid, phosphoric acid, hydroiodic acid, dodecylbenzenesulfonic acid, formic acid, alkylcarboxylic acid, acetic acid, propionic acid, palmitic acid, perfluoroheptanoic acid, oxalic acid, malonic acid, benzoic acid, malic acid, dodecyl sulfuric acid, glycerol-2-phosphoric acid, methyl sulfuric acid, methyl-sulfonic acid, p-toluenesulfonic acid, nitric acid, 2,6-dichloroisonicotinic acid, saccharin, a hydrogen sulfate, or a dihydrogen phosphate.

* * * * *